United States Patent [19]

Lahay

[11] 4,212,305
[45] Jul. 15, 1980

[54] DISPOSABLE FORCEPS

[75] Inventor: Charles A. Lahay, Fayette, Ala.

[73] Assignee: Dart Industries Inc., Los Angeles, Calif.

[21] Appl. No.: 882,676

[22] Filed: Mar. 2, 1978

[51] Int. Cl.³ .......................................... A61B 17/30
[52] U.S. Cl. ...................................... 128/354; 81/43; 128/321
[58] Field of Search ............. 128/321, 322, 346, 354; 81/43

[56] References Cited

U.S. PATENT DOCUMENTS

| | | | |
|---|---|---|---|
| 3,054,182 | 9/1962 | Whitton | 30/179 |
| 3,106,919 | 10/1963 | Churchville | 128/346 |
| 3,140,715 | 7/1964 | Whitton et al. | 128/321 |
| 3,247,852 | 4/1966 | Schneider | 128/346 |
| 3,265,068 | 8/1966 | Holohan | 128/321 |
| 3,302,648 | 2/1967 | Nelson | 128/325 |
| 3,367,336 | 2/1968 | Eizenberg | 128/321 |
| 3,367,337 | 2/1968 | Vavna et al. | 128/325 |
| 3,489,151 | 1/1970 | Eller | 128/365 |
| 3,566,873 | 3/1971 | Melges | 128/305 |
| 3,581,745 | 6/1971 | Eller | 128/356 |
| 3,604,071 | 7/1969 | Reimels | 24/248 L |
| 3,648,702 | 3/1972 | Bean | 128/321 |
| 3,653,389 | 4/1972 | Shannon | 128/354 |
| 3,817,078 | 6/1974 | Reed et al. | 72/392 |
| 3,825,012 | 7/1974 | Nicoll | 128/346 |
| 3,854,482 | 12/1974 | Laugherty et al. | 128/346 |
| 3,879,846 | 4/1975 | Allen | 30/124 |
| 3,906,957 | 9/1975 | Weston | 128/321 |
| 3,977,410 | 8/1976 | Huston et al. | 128/354 |

Primary Examiner—Kyle L. Howell
Assistant Examiner—Michael H. Thaler
Attorney, Agent, or Firm—Leigh B. Taylor

[57] ABSTRACT

A pair of opposed arms include rearward portions which extend tangentially from the cylindrical sidewall of a rigid connecting structure. The rearward portions diverge to substantially parallel intermediate portions having forward portions extending therefrom. A jaw having a face terminating in a nose is carried by each forward portion. Each arm increases in width from the connecting structure to a finger purchase area of the intermediate portion adjacent the forward portion. A rib, integral with each arm, extends from the jaw through the sidewall of the connecting structure and extends therefrom throughout the extent of the sidewall bounded by the arms. In response to compressive force applied to the purchase areas, the arms bend arcuately until the noses of the jaws abut. Continued force causes the jaws to meet in face-to-face relationship.

2 Claims, 8 Drawing Figures

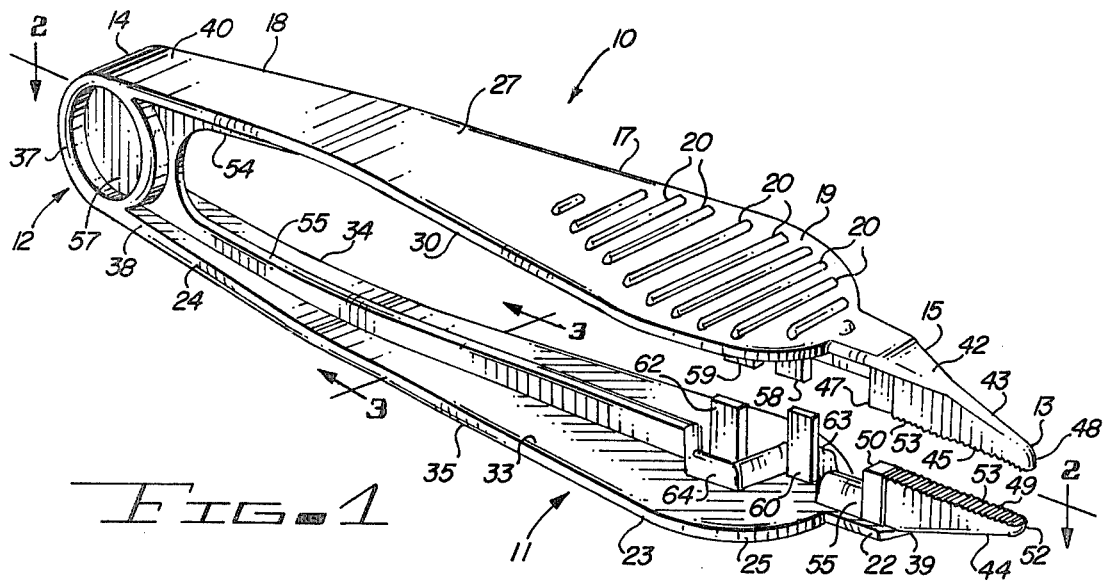
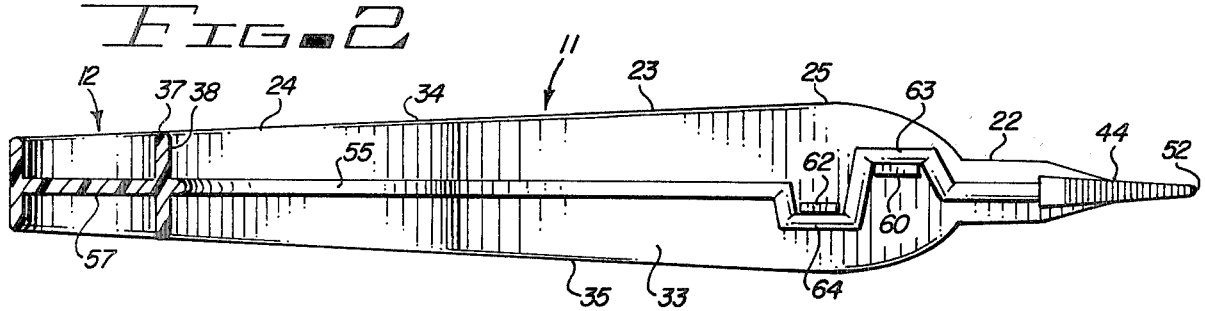
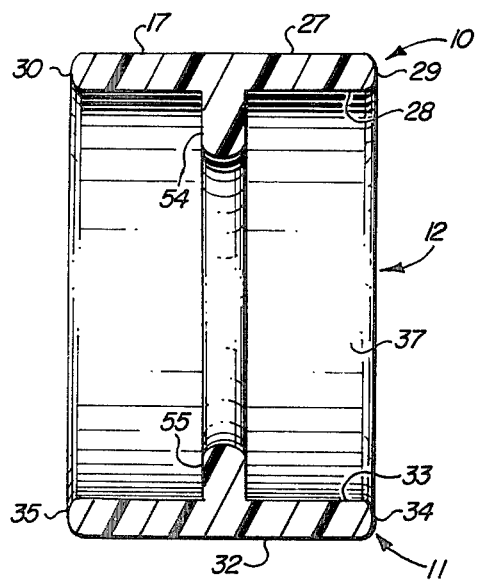
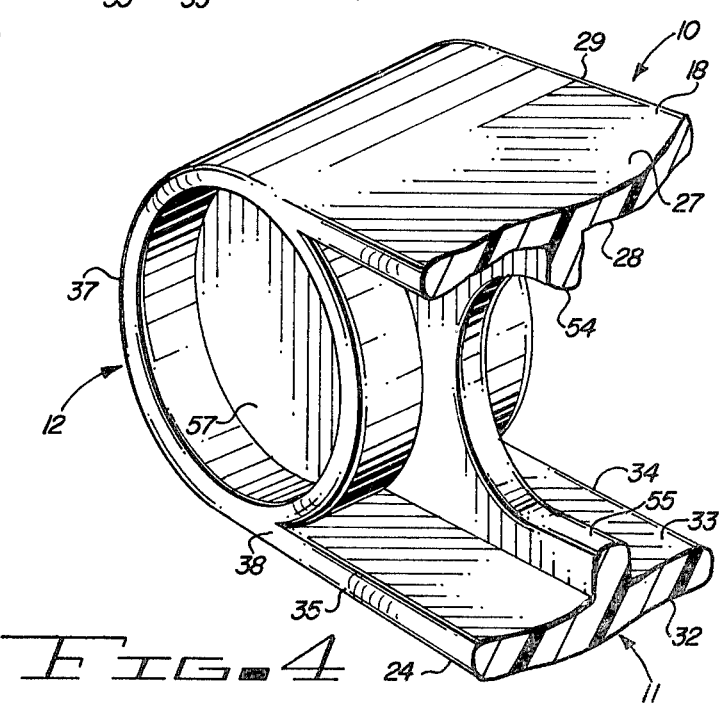

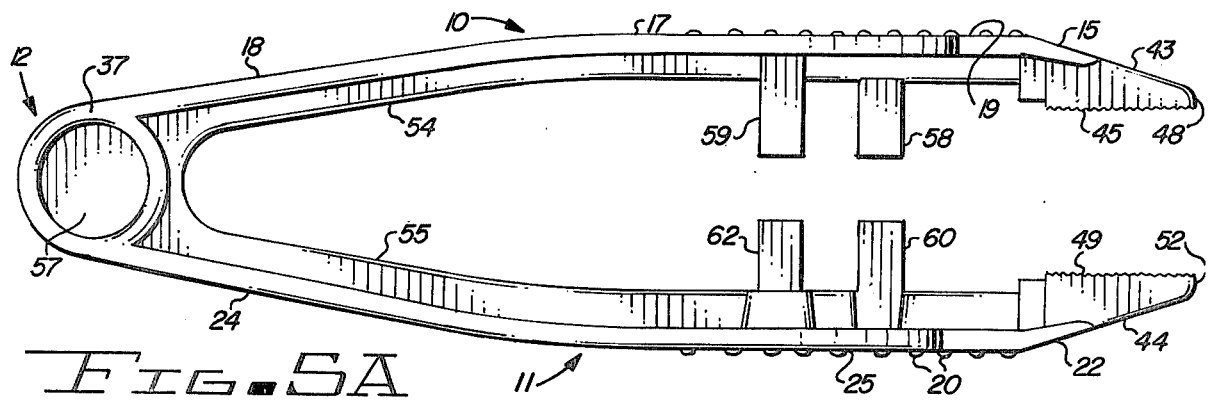
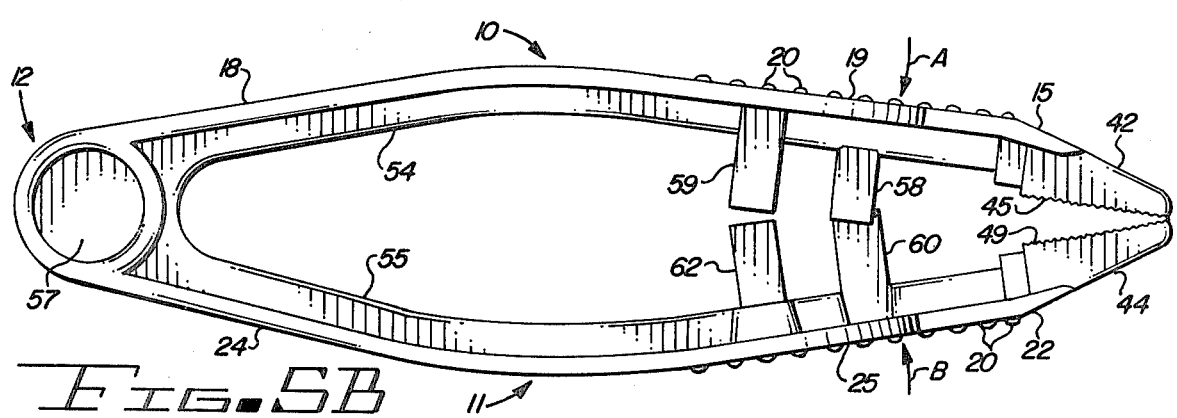
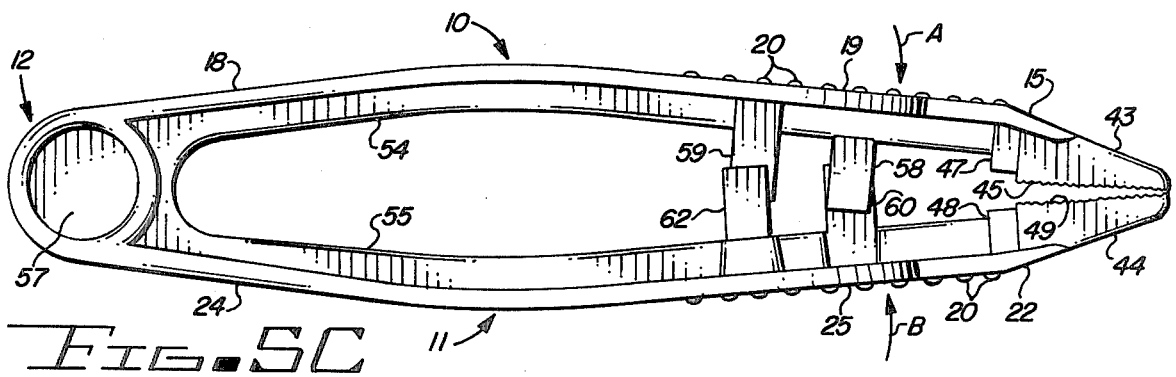
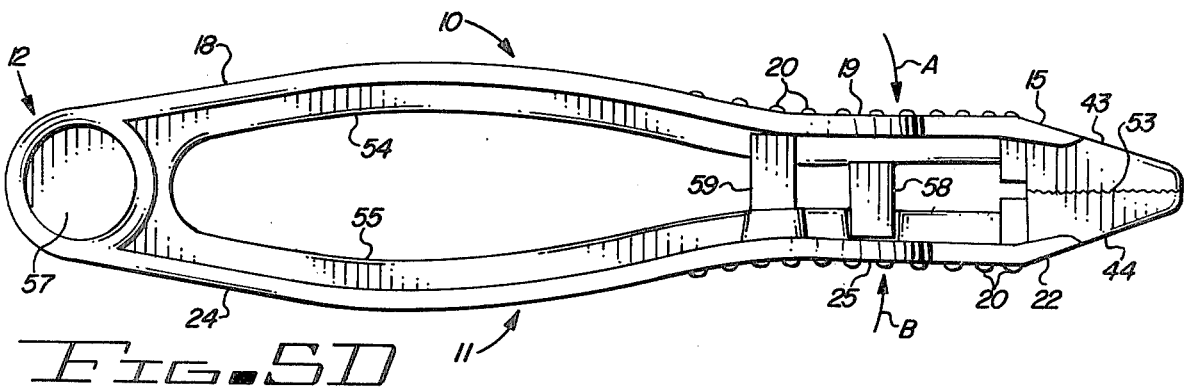

DISPOSABLE FORCEPS

This invention relates to medical and surgical instruments.

More particularly, the present invention concerns forceps of the tweezer type.

In a further aspect, the instant invention concerns a disposable forceps formed as a unitary structure of resilient material.

Forceps are well known instruments within the medical and surgical fields. The devices are commonly used to perform a variety of functions in hospitals, clinics and doctors offices. Physicians and surgeons, for example, usually employ forceps to manipulate dressings, remove sutures and handle other sterile or delicate procedures.

Forceps are commercially available in various sizes and specific physical configurations. In general, forceps of the tweezer type include a pair of elongate arms commonly connected at one end. At the free ends, the arms carry a pair of opposed jaws in normally spaced relationship. In response to compressive force such as applied by the thumb and index finger, the jaws are brought together in a gripping mode.

Traditionally, medical and surgical instruments have been fabricated of stainless steel, which is durable and readily sanitized. Recently, there has been a general trend to products molded of resilient synthetic material, including various plastic compositions. The advantages are several and obvious. Plastic instruments are substantially lighter in weight and considerably less expensive to manufacture. The devices are readily sanitized for re-use or considered disposable at the option of the user.

The recent prior art is replete with various tweezer type forceps which are molded as unitary structures of plastic material. The prior art embodiments, however, have not proven entirely satisfactory. The primary limitation resides in the connecting structure between the arms. Heretofore, it generally has been considered that the connecting structure be weakened by design in order to facilitate movement of the arms. Hence, the connecting structure has been labeled as the "pivot", "fulcum" and other similar terms which denote a movable joint.

Weakened structures such as above are subject to lateral flexing and/or longitudinal misalignment during closure of the forceps. Resultingly, the arms are laterally or longitudinally displaced with subsequent misalignment of the jaws. Efforts to provide a solution to the foregoing problem have resulted in several issued patents which disclose various alignment devices.

Other inherent limitations of the hinge-type connecting structure involves the angle of closure between the jaws. It is generally preferred that the jaws abut at a relatively steep angle to insure initial contact of the noses. Elongate rigid arms, such as taught by the prior art, pivotally connected at one end thereof, undergo relatively minor angular displacement between the normally open position and the closed position of the forceps. To remedy this limitation, the prior art proposes that the jaws be angularly displaced relative the arms or simply that greater separation exists between the arms in the open position. Other shortcomings have also defied solution by the prior art. For example, intricate shapes require expensive molds, increasing unit cost, which is contradictory to the concept of a disposable item. Also, the weakened section absorbing the total bending stress is subject to fatigue and failure. Further, the weakened section decreases the ability of the forceps to return to the normally open position. Other deficiencies, as recognized by those skilled in the art, further limit the desirability of prior art forceps.

It would be highly advantageous therefore to remedy the deficiencies associated with prior art forceps.

Accordingly, it is an object of the present invention to provide an improved forceps of the tweezer type.

Another object of the invention is the provision of a forceps which is fabricated as a unitary structure of a resilient material such as plastic.

And, another object of the invention is to provide a forceps which can be considered disposable or reusable at the option of the user.

Still another object of the invention is the provision of a disposable forceps which is readily sanitized for reuse.

Yet another object of the invention is to provide a forceps having improved structural characteristics.

And still another object of the invention is the provision of a forceps having increased strength and enhanced function.

A further object of the invention is to provide a forceps in which the noses of the jaws first abut at a desirable angle during an initial stage of closing.

And a further object of the invention is the provision of a forceps in which the jaws are brought into face-to-face relationship during a terminal stage of closure.

Yet a further object of the invention is to provide a forceps in which bending moment is imparted to the arms during closure.

And yet a further object of the invention is the provision of a forceps of the above type which is adapted to be readily mass produced at a substantially low cost, yet is relatively durable.

Briefly, to achieve the desired objects of the present invention in accordance with a preferred embodiment thereof first provided is a pair of opposed elongate arms. Each arm includes a substantially straight intermediate portion having a substantially straight rearward portion extending in one direction therefrom and having a terminal end and a substantially straight forward portion extending in the other direction therefrom and having a terminal end. The intermediate portions are substantially parallel. The rearward portions converge from the intermediate portions to a rigid connecting structure. A generally central rib extends inwardly along each arm from the jaw to and through the connecting structure.

Each arm includes a purchase area carried by the intermediate portion near the forward portion. Upon the application of compressive force to the purchase areas, arcuate bending moment occurs in each arm between the purchase areas and the rigid structure. Resultingly, the arms move one toward the other until the noses of the jaws abut. Continued application of the compressive force causes the arms to flex inwardly substantially in the area of the intermediate sections until the faces of the jaws abut.

In a further embodiment, the rigid connecting structure is in the form of a generally cylindrical sidewall. The rearward portions of the arms extend tangentially from the sidewall and have a width at the terminal end substantially equal to the width of the sidewall. The arms increase in width from the connecting structure to proximate the purchase area. The ribs increase in cross-sectional area at the approach to the sidewall and extend therethrough.

The foregoing and further and more specific objects and advantages of the instant invention will become readily apparent to those skilled in the art from the following detailed description of a preferred embodiment thereof taken in conjunction with the drawings in which:

FIG. 1 is a perspective view of a forceps of the tweezer type constructed in accordance with the teachings of the instant invention;

FIG. 2 is a horizontal sectional view taken along the line 2—2 of FIG. 1 and further illustrating one of the arms;

FIG. 3 is an enlarged vertical sectional view taken along the line 3—3 of FIG. 1 and showing additional structure associated with the arms;

FIG. 4 is an enlarged fragmentary perspective view especially illustrating the connecting structure between the arms;

FIG. 5A is an elevation view of the forceps of FIG. 1 as it would appear in the normally open position;

FIG. 5B is a view generally corresponding to the view of FIG. 5A and showing the device thereof as it would appear during an initial stage of closing;

FIG. 5C is a view generally corresponding to the view of FIG. 5A and showing the device thereof during an intermediate stage of closing; and FIG. 5D is a view generally corresponding to the view of FIG. 5A and showing the device thereof as it would appear during a terminal stage of closing.

Turning now to the drawings in which the same reference numerals indicate corresponding elements throughout the several views, attention is first directed to FIG. 1 which shows a forceps of the tweezer type embodying the principles of the instant invention and including a pair of opposed elongate arms generally designated by the reference characters 10 and 11 joined by a connecting structure generally designated by the reference character 12. For purposes of reference, the forceps are considered to have a forward end 13 and a rearward end 14.

Arm 10 has a forward portion 15, intermediate portion 17 and rearward portion 18. Each of the portions 15, 17 and 18 is substantially straight. Intermediate portion 17 has a finger purchase area 19 proximate the forward end thereof, as generally identified by the transverse raised parallel ribs 20. Arm 11, being substantially a mirror image of arm 10, includes substantially straight forward, intermediate and rearward portions 22, 23 and 24, respectively. Intermediate portion 23 has finger purchase area 25 proximate the forward end thereof with ribs similar to those shown at 20. Arm 10 includes outer surface 27, inner surface 28 and opposed edges 29 and 30. Similarly, arm 11 includes outer surface 32, inner surface 33 and opposed edges 34 and 35. Connecting structure 12 includes sidewall 37 which is generally cylindrical about an axis transverse to the forceps.

As best viewed in FIG. 2, rearward portion 24 of arm 11 has a terminal end 38 with a width substantially equal to the length of sidewall 37. Arm 11 increases in width from terminal end 38 to a maximum width in the region of finger purchase area 25. Thereafter, arm 11 decreases in width to terminal end 39 of forward portion 22. Correspondingly, arm 10 increases in width from terminal end 40 of rearward portion 18 to purchase area 10 and decreases in width from purchase area 19 to terminal end 42 of forward portion 15. The width of terminal end 40 corresponds to the length of sidewall 38. Intermediate portions 17 and 23 are substantially parallel in the normally open position, as viewed in FIG. 1. Rearward portions 18 and 24 converge from intermediate portions 17 and 23, respectively, toward connecting structure 12 and blend substantially tangentially into sidewall 37. Further relationships between arms 10 and 11 will be described presently.

Jaws 43 and 44 are carried in opposed relationship by forward portions 15 and 22, respectively. Jaw 43 includes face 45, tail 47 and nose 48. Similarly, jaw 44 includes face 49, tail 50 and nose 52. Each face 45 and 49 is provided with a plurality of teeth 53. In a preferred embodiment of the invention, each tooth has the profile of an isosceles triangle with an apex extending laterally across the respective jaw. The teeth of one jaw are offset from the teeth of the other jaw by a distance equal to one-half the tooth pitch, such that the teeth will mesh when faces 45 and 49 are brought into contact. It is preferred that faces 45 and 49 are parallel when the forceps are in the normally open position, as will be further described as the description ensues.

Reinforcing ribs 54 and 55 are carried by arms 10 and 11, respectively. Rib 54, as viewed in FIG. 3, extends inwardly from inner surface 28 at the approximate midpoint between edges 29 and 30. Rib 55 is generally centrally located between edges 34 and 35 and extends inwardly from inner surface 34. Rib 54 extends along arm 10 from jaw 43 to and through connecting structure 12 and rib 55 extends along arm 11 from jaw 44 to and through connecting structure 12. Approaching connecting structure 12, ribs 54 and 55 converge, increasing in cross-sectional area and joining to a single structure in the form of web 65 and member 57 which pass through and bisect cylindrical sidewall 37, as illustrated in FIG. 4.

Tabs 58 and 59 extend substantially perpendicular from inner surface 28 of arm 10 opposite purchase area 19. Tabs 58 and 59 are spaced along and centered upon rib 54. Tabs 60 and 62 extend substantially perpendicular from inner surface 33 of arm 11. Tabs 60 and 62 are offset laterally to receive tabs 58 and 59 therebetween. In other words, tab 60 is received on one side of tab 58, while tab 62 is received upon the opposite side of tab 59. Rib 55 includes first offset 63 and second offset 64, which accommodate tabs 60 and 62, respectively, and allow tabs 58 and 59 to abut inner surface 33 as the forceps are compressed into the fully closed position, as will be described hereinafter in greater detail.

FIG. 5A illustrates the forceps of the instant invention in the normally open relaxed position. Intermediate sections 17 and 23 are parallel, as are faces 45 and 49 of jaws 43 and 44, respectively. Forceps of the tweezer type are usually manipulated by the user's index and forefinger, which generate compressive force to effect a closing action. In response to compressive force, represented by arrows A and B, applied to purchase areas 19 and 25, respectively, arcuate bending moment is imparted to arms 10 and 11. With limited application of compressive force the forceps are brought to the initial stage of closing, wherein noses 48 and 52 are in contact. The bending movement is primarily opposed by ribs 54 and 55. Since connecting structure 12 is rigid and since ribs 54 and 55 increase in cross-sectional area and finally join as web 65 in the region of connecting structure 12, localized bending is retarded. Localized bending is further retarded throughout the length of arms 10 and 11 due to the uniform cross-section of ribs 54 and 55. Likewise, the combination of web 65 with connecting structure 12 tends to insure both the lateral and longitudinal alignment of arms 10 and 11 so that faces 45 and 49 of jaws 43 and 44 mesh properly. The arcuate bending of arms 10 and 11 results in a rather steep angle between faces 45 and 49 when noses 48 and 42 are abutted, as particularly illustrated in FIG. 5B. Function as described will result when the device is fabricated as a unitary item of various molded plastics, such as glass filled acrylonitrile-butabiene-styrene or equivalent compounds as will occur to those skilled in the art.

In response to continued application of compressive force, as illustrated by arrows A and B at purchase areas 19 and 25, respectively, the arcuation of arms 10 and 11, especially in the area of intermediate portions 17 and 23 and forward portions 15 and 22, begins to reverse. Resultingly, the angle between faces 45 and 49 is decreased, as illustrated in FIG. 5C. The application of compressive force can be continued, as seen in FIG. 5D, until tabs 58 and 59 abut inner surface 33 of arm 11 and tabs 60 and 62 abut inner surface 33 of arm 10, bringing together faces 45 and 49 of jaws 43 and 44, respectively, with teeth 53 in mesh as depicted in FIG. 5D. The abutment of tabs 58 and 59 against surface 33 and the abutment of tabs 60 and 62 against surface 28 prevent further movement of arm 10 toward arm 11. The limit of movement of arm 10 toward arm 11 prevents greater force from being exerted at tails 47 and 50 than noses 48 and 52, which otherwise would tend to separate noses 48 and 52.

The stress applied to the forceps of the instant invention during movement from the relaxed position, as shown in FIG. 5A, to the fully closed position, as illustrated in FIG. 5D, is substantially uniform throughout the length of each arm 10 and 11. It will be appreciated, therefore, that the arms are of uniform strength and not subject to fatigue at a predetermined weakened area. It will also be appreciated, for the same reasons, that a high degree of control is available over the manipulation of the forceps wherein the jaws close in direct proportion to the amount of compressive force applied, and conversely opened in direct proportion to the amount of compressive force released. Further, it is noted that the relative components will assume the position, as illustrated in FIG. 5A, upon the removal of all compressive force. It is also noted that, due to the unique construction of the arms, lateral flexing is minimal, thereby negating the importance of tabs 58, 59, 60 and 62 as lateral stabilizers.

Various changes and modifications to the device herein chosen for purposes of illustration will readily occur to those skilled in the art. For example, while connecting structure 12 is shown as having a generally cylindrical sidewall, other configurations, including a solid member, are envisioned as functionally equivalent. Similarly, forward end 13 is tapered to a relatively narrow profile. This is especially useful for intricate work, such as removing sutures. Other configurations, such as blunt, rounded, etc. are better adapted for other uses. Other features, such as the teeth and profile of the arms, are also subject to the option of the manufacturer. To the extent that such modifications and variations do not depart from the spirit of the invention, they are intended to be included within the scope thereof, which is limited only by a fair interpretation of the appended claims.

Having fully described and disclosed the instant invention and a preferred embodiment thereof in such clear and concise terms as to enable those skilled in the art to understand and practice the same, the invention claimed is:

I claim:

1. In a forceps of the tweezer type fabricated of a plastic material and having integrally connected elements to provide a unitary structure, improvements therein comprising:
    (a) a pair of opposed arms, each said arm including:
        i. a substantially straight intermediate portion,
        ii. a substantially straight rearward portion extending in one direction from said intermediate portion and having a terminal end, and
        iii. a substantially straight forward portion extending in the other direction from said intermediate portion and having a terminal end,
        said intermediate portions being substantially parallel and
        said rearward portions being in converging relationship from said intermediate portions;
    (b) a rigid structure connecting said rearward portions at the terminal ends thereof;
    (c) a jaw carried by each said forward portion and having a face terminating in the nose;
    (d) a generally central rib extending inwardly from each arm and connected at one end to said jaw and connected at the other end to said rigid structure,
    (e) a generally cylindrical wall of a width substantially equal to the width of the terminal ends of said rearward portions, which portions extend substantially tangentially therefrom, said cylindrical wall further having an intermediate transverse partition which is substantially a continuation of said ribs, and
    (f) a purchase area carried by each said intermediate portion nearer said forward portion than said rearward portion,
whereby, upon compressive force being applied to said purchase areas, arcuate bending moment occurs in said arms between said purchase areas and said rigid structure and said arms move, one toward the other, until the noses of said jaws abut, and whereupon continued application of said compressive force causes said arms to flex inwardly, substantially in the area of said intermediate section, until the faces of said jaws abut.

2. The forceps of claim 1, wherein said rigid structure is comprised of a generally cylindrical wall bisected by a substantially planar member that is an extension of said ribs.

* * * * *